(12) United States Patent
Marston et al.

(10) Patent No.: US 7,223,836 B2
(45) Date of Patent: May 29, 2007

(54) PEPTIDES FOR CHLAMYDOPHILA PNEUMONIAE VACCINE AND DIAGNOSIS

(75) Inventors: Eric L. Marston, Atlanta, GA (US); Jackie S. Sampson, College Park, GA (US); George M. Carlone, Stone Mountain, GA (US); Edwin W. Ades, Atlanta, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 301 days.

(21) Appl. No.: 10/479,503

(22) PCT Filed: May 31, 2002

(86) PCT No.: PCT/US02/17278

§ 371 (c)(1),
(2), (4) Date: Dec. 2, 2003

(87) PCT Pub. No.: WO02/099039

PCT Pub. Date: Dec. 12, 2002

(65) Prior Publication Data

US 2005/0261476 A1 Nov. 24, 2005

Related U.S. Application Data

(60) Provisional application No. 60/296,496, filed on Jun. 5, 2001.

(51) Int. Cl.
*A61K 38/00* (2006.01)
*A61K 39/118* (2006.01)
*C07K 1/00* (2006.01)
*C12P 21/04* (2006.01)
*G01N 33/53* (2006.01)

(52) U.S. Cl. ............. 530/300; 530/350; 530/402; 530/811; 530/814; 530/820; 530/825; 435/69.7; 435/184; 435/7.1; 424/190.1; 424/192.1; 424/234.1; 424/263.1; 536/23.7

(58) Field of Classification Search ............ 530/300, 530/350, 402, 811, 814, 820, 825; 435/69.7, 435/184.1, 187.1, 184; 424/190.1, 192.1, 424/234.1, 263.1; 536/23.7
See application file for complete search history.

(56) References Cited

U.S. PATENT DOCUMENTS 5,281,518 A 1/1994 Campbell et al.
5,350,673 A 9/1994 Campbell et al.
5,439,881 A 8/1995 Narva et al.
5,686,068 A 11/1997 Melief et al.
5,693,488 A 12/1997 Fang et al.
5,837,460 A 11/1998 Von Feldt et al.
5,869,608 A 2/1999 Caldwell et al.
6,030,799 A 2/2000 Agabian et al.
6,034,230 A 3/2000 Bachmaier et al.
6,146,839 A 11/2000 Morikawa et al.
6,165,478 A 12/2000 Izutsu et al.

FOREIGN PATENT DOCUMENTS

WO WO 99/45954 A 9/1999

OTHER PUBLICATIONS

Rudinger et al, in "Peptide Hormones", edited by Parsons, J.A., University Park Press, Jun. 1976, p. 1-6.*
Jobling et al. (Mol. Microbiol. 1991, 5(7): 1755-67.*
Moazed et al., *J. Infectious Dis.* 175:883-890, 1997.
Murdin et al., *J. Infectious Dis.* 181(Supp. 3):S544-S551, 2000.
Wong et al., *J. Clin. Microbiol.* 30(7):1625-1630, 1992.
Yang et al., *Infection & Immunity* 61(5):2037-2040, 1993.
International Search Report from PCT/US02/17278.
Marston et al., "Discovery and characterization of a novel immunogenic Chylamydophila pneumoniae peptide reactive with murine monoclonal and human serum antibodies," *41st ICAAC Abstracts*, Chicago, IL, Sep. 22-25, 2001.
Marston et al., "Newly Characterized Species-Specific Immunogenic Chlamydophila pneumonia Peptide Reactive with Murine Monoclonal and Human Serum Antibodies," *Clinical and Diagnostic Laboratory Immunology*, 9(2):446-452, 2002.
Naidu et al., "An immunogenic epitope of Chlamydia pneumoniae from a random phage display peptide library is reactive with both monoclonal antibody and patients sera," *Immunology Letters*, 62(2):111-115, 1998.
Srivastava et al., "Selection of an Immunogenic and Protective Epitope of the PsaA Protein of Streptococcus pneumoniae Using a Phage Display Library," *Hybridoma*, 19(1):23-31, 2000.
Wong et al., "Efficient Culture of Chlamydia pneumoniae with Cell Lines Derived from the Human Respiratory Tract," *Journal of Clinical Microbiology*, 30(7):1625-1630, 1992.
Supplementary European Search Report issued on Sep. 19, 2005 for European Patent Application No. 02749546.4.

* cited by examiner

*Primary Examiner*—Susan Ungar
*Assistant Examiner*—Padma Baskar
(74) *Attorney, Agent, or Firm*—Klarquist Sparkman, LLP

(57) ABSTRACT

Peptides are disclosed that include SEQ ID NO:1, SEQ ID NO: 2, SEQ ID NO:3, SEQ ID NO:4, SEQ ID NO:5, and SEQ ID NO:6, or a conservative variant or mimic thereof, wherein the conservative variant or mimic specifically binds an antibody that specifically binds SEQ ID NO:1, SEQ ID NO: 2, SEQ ID NO:3, SEQ ID NO:4, SEQ ID NO:5, SEQ ID or NO:6. These peptides are of use in generating an immune response against *C. pneumoniae*, or in preventing infection with against *C. pneumoniae*.

16 Claims, 4 Drawing Sheets

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Immunogenic polypeptide epitope that binds a C.
      pneumoniae antibody.

<400> SEQUENCE: 1

Arg Arg Leu Gly Arg Gln Thr Tyr Asp Asn Glu Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Immunogenic polypeptide epitope that binds a C.
      pneumoniae antibody.

<400> SEQUENCE: 2

His Asp Glu Gly Arg Gln Ile Ile Gln Phe Glu Glu
1               5                   10

<210> SEQ ID NO 3
<211> LENGTH: 12
<212> TYPE: PRT
<213> ORGANISM: Artificial Sequence
```

-continued

```
<220> FEATURE:
<223> OTHER INFORMATION: Immunogenic polypeptide epitope that binds a C.
      pneumoniae antibody.

<400> SEQUENCE: 3

Leu Arg Asn Cys Glu Gln Asp Phe Phe Thr Leu Asn
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Immunogenic polypeptide epitope that binds a C.
      pneumoniae antibody.

<400> SEQUENCE: 4

Pro Asn Glu Pro Asp Asp Leu Ala Leu Met Arg Ile Ile Arg Ile
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: Immunogenic polypeptide epitope that binds a C.
      pneumoniae antibody.

<400> SEQUENCE: 5

Ala Phe Ala Gln Ala Pro Thr His Gln Leu Ser Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Immunogenic polypeptide epitope that binds a C.
      pneumoniae antibody.

<400> SEQUENCE: 6

Glu Ser Asn Pro Val Asp Gly Ala His Leu Ser Leu
1               5                   10
```

PEPTIDES FOR CHLAMYDOPHILA PNEUMONIAE VACCINE AND DIAGNOSIS

CROSS REFERENCE TO RELATED APPLICATIONS

This is the U.S. National Stage of International Application No. PCT/US02/17278, filed May 31, 2003, which was published in English under PCT Article 21(2), which in turn claims the benefit of U.S. Provisional Application No. 60/296,496, filed Jun. 5, 2001. Both applications are incorporated herein in their entirety.

FIELD OF THE INVENTION

This application relates to the field of *Chlamydophila pneumoniae*, specifically to peptide epitopes of *Chlamydophila pneumoniae*, and to use of phage display to isolate peptide epitopes.

BACKGROUND

*Chlamydophila pneumoniae* (*C. pneumoniae*), formerly known as *Chlamydia pneumoniae* (Everett et al. 1999), was first isolated in 1965 and identified 15 years later. (Grayston 2000) and is established as an etiologic agent of respiratory tract diseases and related sequelae (Chirgwin et al. 1991, Grayston et al. 1989, Grayston et al. 1990, Grayston et al. 1994, Gnarpe 1999). *C. pneumoniae* has been linked to asthma (Hahn 2000), Guillain-Barré syndrome (Haidl et al. 1992), endocarditis, atherosclerotic vascular disease (Ramirez et al. 1996), Kawasaki disease (Normann et al. 1999), chronic obstructive pulmonary disease (Verkooyen 1997, Miyashita et al. 1998), sarcoidosis (Laurila 1997), reactive arthritis (Hannu et al. 1999), and multiple sclerosis (Sriram et al. 1999). *Chlamydophila* are Gram-negative obligate intracellular bacteria having a biphasic life cycle, consisting of a metabolically inert infectious elementary body (EB) and a metabolically active reticulate body (RB).

*C. pneumoniae* is a respiratory pathogen believed to cause 5–20% of community-acquired pneumonias and 5% of bronchitis and sinusitis in adults and children (Jolcinen 2001, Wubbel 1999, Ouchi 1999, Porath 1997, Schito 1994). Recent studies suggest that not only does this organism rank as the 3$^{rd}$ most common cause of pneumonia, but also may play a more significant role in the pathogenesis of several chronic diseases including asthma and atherosclerosis. Seroepidemiology has shown that most *C. pneumoniae* infections are asymptomatic (Aldous, Wang, Foy, Grayston 1990). Regional and international serology-based epidemiologic studies of *C. pneumoniae* have shown a high prevalence and ubiquitous infection. These studies have indicated that most people have had their first *C. pneumoniae* infection before age 20, and reinfection is common.

The biphasic life cycle and intracellular host cell parasitism of *chlamydia* could allow for maintenance of a chronic infection. It is well established that *C. psittici* can persist in mammals and birds lifelong, and only occasionally cause disease, most often after some form of stress induction. *C. pneumoniae* has been demonstrated to multiply in macrophages, endothelia, smooth muscle cells, etc. in vitro. *C. pneumoniae* multiplication has been associated with cytokine production and induction of adhesions (Kaukoranta et al. 1996, Dechend et al. 1999).

Many laboratory methods have been developed for the diagnosis of *C. pneumoniae* infection, including primary isolation of the organism in cell culture, serological assays, immunohistochemical assays and polymerase chain reaction (PCR) (Grayston 1992). Despite great effort to improve primary culture techniques of *C. pneumoniae*, isolation and culture still require specialized personnel and substantial laboratory resources. To date, only a few laboratories worldwide have made human isolates.

Serologic and PCR assays are the tools most often applied for routine diagnosis of acute *C. pneumoniae* infection. Serologic assays include complement fixation (CF), micro-immunofluorescence (MIF), enzyme-linked immunosorbant assay (ELISA), and immunobistochemistry (Bames 1989). These assays require significant technical expertise and are subject to investigator interpretation. The MIF test remains the most sensitive assay, the only species-specific assay, and is considered the current "Gold Standard" for determining prevalence of *C. pneumoniae* in populations studied (Verkooyen et al. 1998). The traditional MIF assay relies on the use of whole elementary bodies (EB) as an antigen. Though lacking the necessary species specificity for use as a diagnostic serologic test, indirect immunofluorescence assay (IFA) has been used for culture confirmation of isolates or for laboratory culture standardization. IFA relies on both whole RBs and EBs fixed with methanol as antigen in *C. pneumoniae* infected cell culture. The use of whole *C. pneumoniae* antigen has been observed by investigators to have cross reactivity in certain serologic and immunohistochemical tests (Brade et al. 1990). Thus, there clearly is a need for assays that identify *C. pneumoniae*. In addition, there is a need for novel treatments for *C. pneumoniae* infections such as pneumonia, and vaccines that can prevent such infections.

SUMMARY

In one embodiment, novel substantially purified *C. pneumoniae* polypeptides are provided. The polypeptides are epitopes that specifically bind a *C. pneumoniae* antibody. A novel peptide is disclosed that has a sequence as set forth as SEQ ID NO:1, SEQ ID NO: 2, SEQ ID NO:3, SEQ ID NO:4, SEQ ID NO:5, SEQ ID NO:6, or a conservative variant thereof. In one embodiment, the conservative variant specifically binds an antibody that specifically binds SEQ ID NO:1 SEQ ID NO:2, SEQ ID NO:3, SEQ ID NO:4, SEQ D) NO:5, or SEQ ID NO:6, respectively. Nucleic acids encoding these peptides are disclosed herein, as well as host cells expressing the peptides. These novel peptides are immunogenic.

A novel method is disclosed for determining if antibodies that bind a *C. pneumoniae* peptide are included in a sample. In addition, a method is also disclosed for diagnosing a *C. pneumoniae* infection. Methods are also disclosed for treating or preventing a *C. pneumoniae* infection using a novel *C. pneumoniae* polypeptide, or a nucleic acid encoding the polypeptide.

The foregoing and other objects, features, and advantages will become more apparent from the following detailed description of several embodiments which proceeds with reference to the accompanying figures.

DETAILED DESCRIPTION OF SEVERAL EMBODIMENTS

Figure 1:
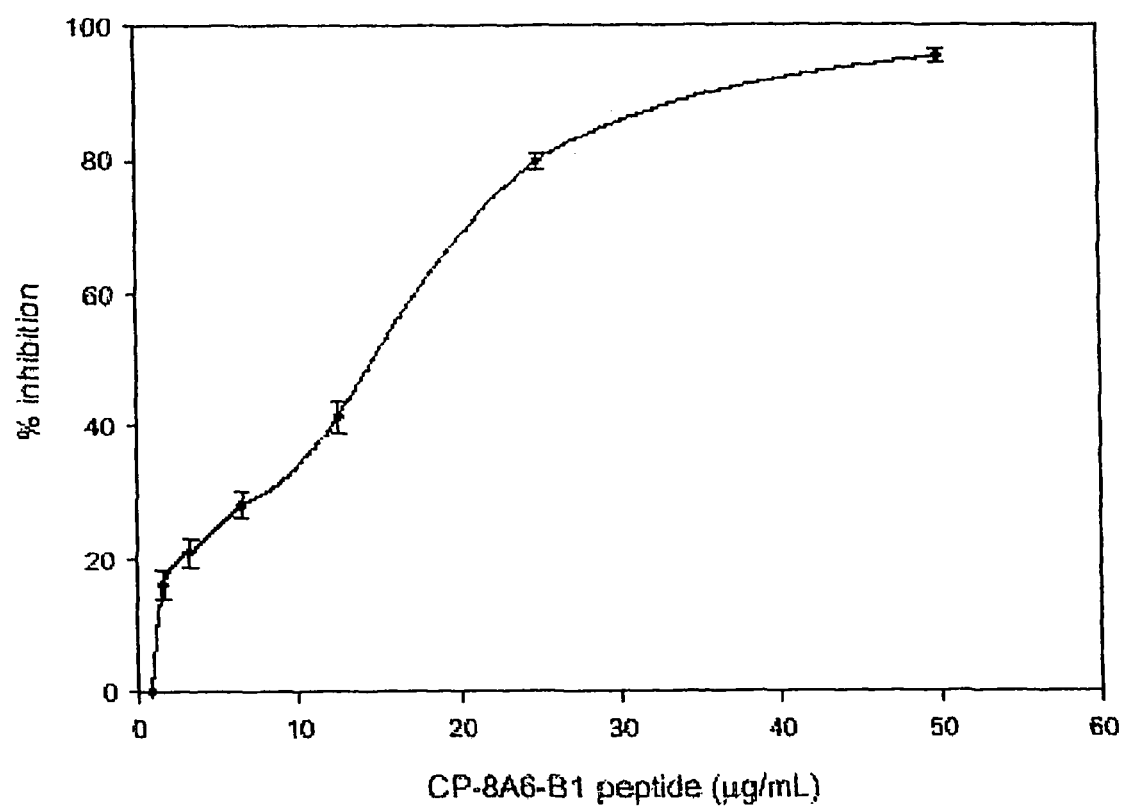
FIG. 1 is a graph of the inhibition of 8A6 mAb reactivity to *C. pneumoniae* by peptide CP-8A6-B1. The graph shows the mean for the percent inhibition of three wells at each concentration of peptide and compared to control wells in which only PBS was added.

Unless otherwise noted, technical terms are used according to conventional usage. Definitions of common terms in molecular biology may be found in Benjamin Lewin, *Genzes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechiziology: a Comprehensive Desk Reference*, published by VCH Publishers, Inc., 1995 (ISBN 1-56081-569-8). U.S. Pat. No. 5,753,500.

The singular forms "a", "an", and "the" refer to one or more than one, unless the context clearly dictates otherwise.

Terms

Animal: Living multi-cellular vertebrate organisms, a category that includes, for example, mammals and birds. The term mammal includes both human and non-human mammals. Similarly, the term "subject" includes both human and veterinary subjects.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Agent: Any substance, including, but not limited to, an antibody, chemical compound, molecule, peptidomimetic, or protein.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Conservative substitutions: A conservative substitution is an amino acid substitution that does not affect the charge, hydrophobicity, or function of a protein or peptide. In one embodiment, a conservative substitution is an amino acid substitution in an antigenic epitope of a *C. pneumoniae* peptide that does not substantially affect the ability of an antibody to bind the peptide. In one embodiment, one conservative substitution is included in the peptide. In another embodiment, two conservative substitutions or less are included in the peptide. In a further embodiment, three conservative substitutions or less are included in the peptide.

Examples of "conservative" amino acid substitutions include, but are not limited to, those listed below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Degenerate variant: A polynucleotide encoding a *C. pneumoniae* polypeptide that includes a sequence that is degenerate as a result of the genetic code. There are 20 natural amino acids, most of which are specified by more than one codon. Therefore, all degenerate nucleotide sequences are included in the invention as long as the amino acid sequence of the *C. pneumoniae* polypeptide encoded by the nucleotide sequence is unchanged.

Epitope: An antigenic determinant. These are particular chemical groups or peptide sequences on a molecule that are antigenic, i.e. that elicit a specific immune response. An antibody binds a particular antigenic epitope.

Expression Control Sequences: Nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term control sequences is intended to include, at a minimum, components whose presence can influence expression, and can also include additional components whose presence is advantageous, for example, leader sequences and fusion partner sequences. Expression control sequences can include a promoter.

Functionally Equivalent: Sequence alterations in an antigen, wherein the antigen with the sequence alterations retains a function of the unaltered antigen, such as it specifically binds an antibody that binds an unaltered form of the antigen. Such sequence alterations can include, but are not limited to, conservative substitutions, deletions, mutations, frameshifts, and insertions. In one embodiment, a given polypeptide binds an antibody, and a functional equivalent is a polypeptide that binds the same antibody. Thus a functional equivalent includes peptides which have the same binding specificity as a polypeptide, and which may be used as a reagent in place of the polypeptide (such as in a diagnostic assay of vaccine). In one embodiment a functional equivalent includes a polypeptide wherein the binding sequence is discontinuous, wherein the antibody binds a linear epitope. Thus, if the peptide sequence is RRLGRQTYDNES (SEQ ID NO:1) a functional equivalent includes discontinuous epitopes, which may can appear as follows (**=any number of intervening amino acids):

NH2-—RRLGRQTYDNES—COOH.

This polypeptide is functionally equivalent to SEQ ID NO:1 if the three dimensional structure of the polypeptide is such that it can bind a monoclonal antibody that binds SEQ ID NO:1.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Isolated: An "isolated" biological component (such as a nucleic acid, peptide or protein) has been substantially separated, produced apart from, or purified away from other biological components in the cell of the organism in which the component naturally occurs, i.e., other chromosomial and extrachromosomal DNA and RNA, and proteins. Nucleic acids, peptides and proteins which have been "isolated" include nucleic acids and proteins purified by standard purification methods. The term also embraces nucleic acids, peptides and proteins prepared by recombinant expression in a host cell as well as chemically synthesized nucleic acids.

Isolated, Purified, Homogeneous Polypeptides: A polypeptide is "isolated" if it has been substantially separated from contaminants, e.g., cellular components (nucleic acids, lipids, carbohydrates, and other polypeptides) that naturally accompany it. Such a polypeptide can also be referred to as "pure" or "homogeneous" or "substantially" pure or homogeneous. A C. pneumoniae is isolated when at least 60–90% by weight of a sample is composed of the polypeptide, for example when 95% or more, or more than 99% of a sample is composed of the polypeptide. Protein purity or homogeneity is indicated, for example, by polyacrylamide gel electrophoresis of a protein sample, followed by visualization of a single polypeptide band upon staining the polyacrylamide gel; high-pressure liquid chromatography; sequencing; or other conventional methods.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphomnuclear leukocytes (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B-cell and T-cells.

Mammal: This term includes both human and non-human mammals. Similarly, the term "subject" includes both human and veterinary subjects.

Mimetic: A molecule (such as an organic chemical compound) that mimics the activity of a protein, such as a C. pneumoniae peptide that specifically binds to a monoclonal antibody, or variants or fusions thereof. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides having substantial specific inhibitory activity or agonist activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs." in Klegerman & Groves, eds., Pharmaceutical Biotechnology, Interpharm Press: Buffalo Grove, Ill., pp. $1^{65}$-174, 1993 and Principles of Pharmacology, (ed. Munson), chapter 102, 1995, for a description of techniques used. In one embodiment, a mimetic mimics C. pneumoniae peptide or protein as it binds to a monoclonal antibody that recognizes the C. pneumoniae peptide or protein.

Nucleic acid: A deoxyribonucleotide or ribonucleotide polymer in either single or double stranded form, and unless otherwise limited, encompasses known analogues, of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 12 amino acids in length.

Peptide Modifications: The present invention includes biologically active peptides that bind a C. pneumoniae antibody. The peptides of the invention include synthetic embodiments of peptides described herein. In addition, analogues (non-peptide organic molecules), derivatives (chemically functionalized peptide molecules obtained starting with the disclosed peptide sequences) and variants (homologs) of these proteins that specifically bind a C. pneumoniae antibody can be utilized in the methods described herein. Each peptide of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or maybe modified to $C_1$–$C_{16}$ alkyl or dialkyl amino or further converted to an amide.

Hydroxyl groups of the peptide side chains may be converted to $C_1$–$C_{16}$ alkoxy or to a $C_1$–$C_{16}$ ester using well-recognized techniques. Phenyl and phenolic rings of the peptide side chains may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the peptide side chains can be extended to homologous $C_2$–$C_4$ alkylenes. Thiolscan be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are also within the scope of the present invention, whereby the three-dimensional arrangement of the chemical constituents of such peptido- and organomimetics mimic the three-dimensional arrangement of the peptide backbone and component amino acid side chains, resulting in such peptido- and organomimetics of the proteins of this invention having measurable or enhanced ability to bind an antibody. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegeman & Groves, eds., 1993, *Pharmaceutical Biotechnology*, Interpharm Press: Buffalo Grove, Ill., pp. 165–174 and *Principles of Pharmacology*) Munson (ed.) 1995, Ch. 102, for descriptions of techniques used in CADD. Also included within the scope of the invention are mimetics prepared using such techniques. In one embodiment, a mimetic mimics the binding of a *C. pneumoniae* peptide or *C. pneumoniae* protein to an antibody.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful in this invention are conventional. *Remington's Pharmaceutical Sciences,* by E. W. Martin, Mack Publishing Co., Easton, Pa., 15th Edition (1975), describes compositions and formulations suitable for pharmaceutical delivery of the peptides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleic acid sequence of any length. Therefore, a polynucleotide includes molecules which are no more than 15, 50, 100, 200 nucleotides in length (oligonucleotides) and also nucleotides as long as a full length cDNA. A "*C. pneumoniae* polynucleotide" encodes a *C. pneumoniae* peptide.

Polypeptide: Any chain of amino acids, regardless of length or post-translational modification (e.g., glycosylation or phosphorylation). In one embodiment, the polypeptide is a *C. pneumoniae* polypeptide, which is any chain of amino acids, regardless of length and post-translational modification, found in a *C. pneumoniae.*

Preventing or treating a disease: "Preventing" a disease refers to inhibiting the full development of a disease, for example preventing pneumonia in a person who is known to have a *C. pneumoniae* infection, or preventing infection with *C. pneumoniae* in a subject exposed to *C. pneumoniae.* "Treatment " refers to a therapeutic intervention that ameliorates a sign or symptom of a disease or pathological condition related to infection of a subject with *C. pneumoniae.*

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g. Bitter et al., *Methods in Enzymology* 153:516–544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used. A polynucleotide encoding a *C. pneumoniae* peptide may be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Similarly, a recombinant protein is one encoded for by a recombinant nucleic acid molecule.

Specific binding agent: An agent that binds substantially only to a defined target. Thus a *C. pneumoniae* specific binding agent is an agent that binds substantially to a *C.*

*pneumoniae* polypeptide. In one embodiment, the specific binding agent is a monoclonal or polyclonal antibody.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a *C. pneumonlae* peptide, disclosed herein, will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237–244,1988; Higgins and Sharp, *CABIOS* 5:151–153, 1989; Corpet et al., *Nucletic Acids Research* 16:10881–10890, 1988; and Pearson and Lipman, *Proc. Natl. Acad. Sci. U.S.A.* 85:2444, 1988. Altschul et al., *Nature Genet.* 6:119–129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Variants of a *C. pneumoniae* peptide are typically characterized by possession of at least 50% sequence identity counted over the full length alignment with the amino acid sequence of *C. pneumoniae* using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 60%, at least 65%, at least 70%, at least 75%, at least 80%, at least 90%, or at least 95%, or 98% sequence identity. When less than the entire sequence is being compared for sequence identity, hiomologs and variants will typically possess at least 75% sequence identity over short windows of 10–20% amino acids, and may possess sequence identities of at least 85% or at least 90%, 95%, or 98% depending on their similarity to the reference sequence. Methods for determining sequence identity over such short windows are described at the website that is maintained by the National Center for Biotechnology Information in Bethesda, Md. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human veterinary subjects, including human and and non-human mammals.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer cell responses. $CD8^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutically active molecule: An agent, such as a *C. pneumoniae* polypeptide that causes induction of an immune response, as measured by clinical response (for example increase in a population of immune cells, or measurable reduction of tumor burden). Therapeutically active molecules can also be made from nucleic acids. Examples of nucleic acid based therapeutically active molecules are a nucleic acid sequence that encodes a *C. pneumoniae* peptide, wherein the nucleic acid sequence is operably linked to a control element such as a promoter. Therapeutically active agents can also include organic or other chemical compounds that mimic the effects of the peptide.

Therapeutically effective dose: A dose sufficient to inhprevent advancement, or to cause regression of the disease, or which is capable of relieving symptoms caused by the disease, such as fever, pain, decreased appetite or any symptom associated with *C. pneumoniae*, or is sufficient to increase the efficacy of another agent, such as an antibiotic.

Transduced and Transformed: A virus or vector "transduces" or "transfects" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transfected: A transfected cell is a cell into which has been introduced a nucleic acid molecule by molecular biology techniques. As used herein, the term transfection encompasses all techniques by which a nucleic acid molecule might be introduced into such a cell, including transfection with viral vectors, transformation with plasmid vectors, and introduction of naked DNA by electroporation, lipofection, and particle gun acceleration.

Transgene: An exogenous nucleic acid sequence supplied by a vector. In one embodiment, a transgene encodes a *C. pneumoniae* polypeptide.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. In one embodiment, a vector is a viral vector. Viral vectors include, but are not limited to, retroviral and adenoviral vectors.

*C. pneumoniae* Polynucleotides and Polypeptides

In one embodiment, novel substantially purified *C. pneumoniae* polypeptides are provided. The polypeptides are epitopes that specifically bind a *C. pneumoniae* antibody.

Specifically, polypeptides are disclosed herein that have an amino acid sequence set forth in SEQ ID NO:1, SEQ ID NO:2, SEQ ID NO:3, SEQ ID NO:4, SEQ ID NO:5, and SEQ ID NO:6. The novel polypeptides are immunogenic, and can be used to detect a C. pneumoniae infection. In addition, these novel polypeptides can be used to produce an immune response against C. pneumoniae in a subject.

One skilled in the art, given the disclosure herein, can purify the novel C. pneumoniae polypeptide using standard techniques for protein purification. The substantially pure polypeptide will yield a single major band on a non-reducing polyacrylamide gel. The purity of the C. pneumoniae polypeptide can also be determined by amino-terminal amino acid sequence analysis.

Minor modifications of the C. pneumoniae polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein as long as an activity of the C. pneumoniae polypeptide, such as the binding of the epitope to an antibody (e.g. a monoclonal antibody), still exists.

Polynucleotides encoding a C. pneumoniae polypeptide are also provided. These polynucleotides include DNA, cDNA and RNA sequences which encode the C. pneumoniae polypeptide. It is understood that all polynucleotides encoding C. pneumoniae polypeptide are also included herein, as long as they encode a polypeptide with the recognized activity, such as the binding to an antibody that recognizes the C. pneumoniae polypeptide. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of C. pneumoniae polypeptide encoded by the nucleotide sequence is functionally unchanged.

The polynucleotides encoding a C. pneumoniae polypeptide include a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double forms of DNA. Also included in the invention are fragments of the above-described nucleic acid sequences that are and are at least 15 bases in length, which is sufficient to permit the fragment to selectively hybridize to DNA that encodes the disclosed C. pneumoniae polypeptide (e.g. a polynucleotide that encodes any one of SEQ ID Nos:1–6 under physiological conditions. The term "selectively hybridize" refers to hybridization under moderately or highly stringent conditions which excludes non-related nucleotide sequences. The nucleotide sequence encoding the disclosed C. pneumoniae polypeptides disclosed herein includes the disclosed sequences, degenerate sequences, and sequences that encode conservative variations thereof.

DNA sequences encoding a disclosed C. pneumoniae polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The C. pneumoniae polynucleotide sequences may be inserted into an expression vector including, but not limited to a plasmid, virus or other vehicle that has been manipulated by insertion or incorporation of the C. pneumoniae genetic sequences. Polynucleotide sequences which encode a C. pneumoniae polypeptide can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers., transcription terminators, a start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

The polynucleotide encoding C. pneumoniae polypeptide may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences encoding a *C. pneumoniae* polypeptide can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences encoding a *C. pneumoniae* polypeptide.

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host-cell if desired, or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding a *C. pneumoniae* polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors,* Cold Spring Harbor Laboratory, Gluzman ed., 1982).

Isolation and purification of recombinantly expressed polypeptide may be carried out by conventional means including preparative chromatography and immunological separations involving monoclonal or polyclonal antibodies, such as, for example, mAb 8A6.

Assays for *C. pneumoniae* Infection

Methods for assaying for *C. pneumoniae* infection of a subject are disclosed herein. In one embodiment, the *C. pneumoniae* polypeptide is adsorbed onto a solid substrate. In one embodiment, the solid substrate is polystyrene beads or plates. The substrate is thereafter contacted with a substance, such as protein containing solution, that saturates the binding sites thereon. Specific, non-limiting examples of a protein containing solution are a solution made from powdered milk or serum albumin, such as bovine serum albumin. The substrate is then washed with a buffer. A specimen, such as sera, a cell, tissue, blood, plasma, urine, semen, saliva, sputum, cerebrospinal fluid, lacrimal fluid, lymph fluid, synovial fluid, pleural fluid, is then added to the substrate, and the combined specimen and substrate are incubated for a sufficient time to allow specific binding. Specific binding of components of the specimen, for example, antibodies, that specifically bind the *C. pneumoniae* polypeptide are then detected using any means known to one of skill in the art. In one embodiment, a labeled antibody is used to detect the component of the specimen that binds the *C. pneumoniae* polypeptide. The label can be a radiolabel (e.g. $^{125}I$, an enzymatic label (e.g. alkaline phosphatase or horseradish peroxidase), or a fluorescent label (e.g. fluoroscein isothiocyanate). Specific non-limiting examples of assays of use include a radioimmunoassay (RIA) and an enzyme linked immune assay (ELISA). Detection systems for these labels are known to one of skill in the art. Binding of the specimen to the *C. pneumoniae* polypeptide, as indicated by the presence of the marker, indicates infection with *C. pneumoniae.*

In another embodiment, the specimen is adsorbed onto a solid substrate containing binding sites for polypeptides, such as antibody molecules in one embodiment, the solid substrate is polystyrene beads or plates. The substrate is thereafter contacted with a substance, such as protein containing solution, that saturates the binding sites thereon. The substrate is then washed with a buffer. A solution of *C. pneumoniae* polypeptide is then added to the bound specimens. In one embodiment, the *C. pneumoniae* polypeptide is directly labeled. The labeling of *C. pneumoniae* polypeptide can be brought about by use of any marker, such as by incorporation of a radioactive atom or group, or by coupling this component to an enzyme, a dyestuff, e.g., chromophoric moiety or a fluorescent group. The enzymes of use are those which can be calorimetrically, spectrophotometrically, or fluorimetrically determined. Non-limiting examples of enzymes for use in the present invention include enzymes from the group of oxidoreductases, such as catalase, peroxidase, glucose oxidase, beta-glucuronidase, beta-D-glucosidase, beta-D-galactosidase, urease and galactose oxidase. Labeled *C. pneumoniae* polypeptide is thus incubated with the solid substrate, any unbound labeled *C. pneumoniae* polypeptide is removed by washing, and the bound labeled *C. pneumoniae* polypeptide is detected by an appropriate means. Binding of the labeled *C. pneumoniae* polypeptide to the specimen is indicative of infection with *C. pneumoniae.*

In another embodiment, the *C. pneumoniae* polypeptide is unlabeled, and an additional detection reagent is used to detect *C. pneumoniae* polypeptide. As described above, the detection reagent includes a labeled antibody that binds the *C. pneumoniae* polypeptide. In one specific, non-limiting example, the antibody is mAb 8A6, and the label is an enzymatic, fluorescent or a radiolabel.

Competitive binding assays are also of use in detecting infection with *C. pneumoniae*. One of skill in the art, given the *C. pneumoniae* polypeptides disclosed herein, will readily be able to design additional assays, such as competitive binding assays, of use in detecting *C. pnuemoniae* infection.

In general, the incubation steps utilized in carrying out the procedures can be performed in a known manner, such as by incubating at temperatures between about 4° C. and about 25° C., for about 30 minutes to about 48 hours. Washings can be included with an aqueous solution such as a buffer, wherein the buffer is from about pH 6 to about pH 8, such as by using an isotonic saline solution of a pH of about 7.

In another embodiment, the *C. pneumoniae* polypeptides disclosed herein can be included in a diagnostic test kit. For example, a diagnostic test kit for detecting antibodies to a *C. pneumoniae* polypeptide in a test sample would include a solid substrate having adsorbed thereon a *C. pneumoniae* polypeptide or a specified amount of a *C. pneumoniae* polypeptide. In other embodiments, the kit includes written instructions and/or a container including a specified amount of labeled antibodies to immunoglobulins, such as IgG or IgM. In one embodiment, the labeled antibodies detect human immunoglobulins, such as IgG or IgM, which are fluorescently labeled, enzymatically labeled, or radiolabeled. Labeled antibodies used in the above-described test kits can be packaged in either solution form, or in lyophilized forms suitable for reconstitution.

In another embodiment the test kit includes a specified amount of a *C. pneumoniae* polypeptide described herein in a container, and written instructions. In one embodiment, the *C. pneumoniae* polypeptide is directly labeled. In another embodiment, the *C. pneumoniae* polypeptide is unlabelled. In a further embodiment, the *C. pneumoniae* polypeptide is unlabeled, and a container is included with a detection reagent that specifically binds the *C. pneumoniae* polypeptide, such as a labeled monoclonal antibody. The kit may also optionally include a solid substrate for binding the specimen.

The above described process and test kit for detection of antibodies to the *C. pneumoniae* polypeptide can be utilized in many applications, including, but not limited to detecting *C. pneumoniae* infection in a subject by taking a body fluid from the patient and applying the above described test or using the above described test kit. The bodily fluid includes, but is not limited to a cell, tissue, blood, plasma, urine, semen, saliva, sputum, cerebrospinal fluid, lacrimal fluid, lymph fluid, synovial fluid, pleural fluid, or serum sample. In another embodiment, the described process and test kit are used for detecting the presence of *C. pneumoniae* in a tissue culture sample. In a further embodiment, the tests and kits disclosed herein can be used to detect the efficacy of a therapeutic treatment in a subject. In yet another embodiment, the tests and kits disclosed herein can also be used to assess a primary infection with *C. pneumoniae* or to predict recovery from *C. pneumoniae* infection by taking a body fluid from an infected patient and applying the above described detection procedures.

The above described test procedure and test kit for antibody detection can be used for making qualitative comparisons between different *C. pneumoniae* polypeptide vaccines by taking serum from vaccinated patients and then utilizing the above-described test procedure or kit for antibody detection. In general all known immunoassays using this antigen as reagent can be performed using the synthetic peptides disclosed herein. Generally all known immunoassays using antibody containing serum or reagents can be also performed using antibody serum produced through the use of a synthetic peptide of this invention. These immunoassays included all those disclosed by Langone and Van Vunakis, Methods of Enzymology, Academic Press, Volumes 70, 73 and 74. Those assays disclosed in the disclosures of the following U.S. Pat. Nos. 4,459,359; 4,343,896; 4,331,761; 4,292,403; 4,228,240; 4,157,280; 4,152,411; 4,169,012; 4,016,043; 3,839,153; 3,654,090 and Re 31,006 and volumes 70, 73 and 74 of Methods of Enzymology.

*C. pneumoniae* Polypeptides and Nucleic Acids Encoding *C. pneumoniae* Polypeptides as Immunogenic Compositions In one embodiment, a method of treating a subject with a *C. pneumoniae* infection is provided, or preventing or inhibiting infection, or the development of clinical disease. Alternatively, the method can be used to inhibit the progress of an already existing infection. The method includes administering to the subject a therapeutically effective amount of *C. pneumoniae* polypeptide, thereby treating or preventing the infection, or retarding or reversing clinical disease.

In forming a composition for generating an immune response in a subject, or for vaccinating a subject, a *C. pneumoniae* polypeptide, or a derivative or variant thereof, is utilized. Analogs involving amino acid deletions, amino acid replacements, or by isostereomer (a modified amino acid that bears close structural and spatial similarity to the original amino acid) substitutions, isostereomer additions, and amino acid additions can be utilized, so long as the sequences elicit antibodies recognizing the *C. pneumoniae* polypeptide.

In the formation of a peptide derived from natural sources, a protein including an amino acid sequence described herein is subject to selective proteolysis. Selective proteolysis includes splitting the protein with chemical reagents or enzymes. Alternatively, a *C. pneumoniae* polypeptide as described herein can be chemically synthesized. In one embodiment, the peptide is synthesized in proper synthetic configuration to be recognized by monoclonal antibody mAb A86 (Wong et al., J. Clin. Microbiol. 30:1625–30, 1992, herein incorporated by reference).

The length of the amino acid sequence produced can depend on the method of producing the sequence. If the sequence is made by assembling amino acids by chemical means, the sequence would not exceed, for example, about 50, or would not exceed about 40, or would not exceed about 30 amino acids. If the synthetic peptide is made by translating a nucleic acid, the peptide can be any length, including, for example, about 100 amino acids or more. However, the peptide can also be shorter, for example, no more than 50, no more than 40, or no more than 30 amino acids.

The *C. pneumoniae* polypeptide can also be engineered to include other amino acids, such as residues of various moieties, such as additional amino acid segments or polysaccharides. In addition, an amino acid chain corresponding to an additional antigen or immunogen can be included. Thus, an immune response to more than one antigen can be induced by immunization. Specific non-limiting examples of antigens or immunogens include, but are not limited to, antigens of hepatitis B, measles, influenza, smallpox, polio, or diptheria. These additional amino acid sequences can be of varying length.

The sequences of amino acids can be interconnected with one another such as by cross-linking or can be bound together covalently. Alternatively, an immunogenic composition can be an admixture with other proteins that are known immunogens. In one embodiment, the peptides included in the composition are capable of forming neutralizing antibodies to the *C. pneumoniae* polypeptide.

A carrier may be provided for the *C. pneumoniae* polypeptides disclosed herein. However, a carrier may not be required to induce an immune response to the *C. pneumoniae* polypeptide. A "carrier" is a physiologically acceptable mass to which the *C. pneumoniae* polypeptide is attached and which is expected to enhance the immune response. In one embodiment, a carrier is a chain of amino acids or other moieties. In another embodiment, a carrier is a dimer, oligomer, or higher molecular weight polymer of a sequence of amino acids of a *C. pneumoniae* polypeptide. In other words, the *C. pneumoniae* polypeptide can be formed from naturally available materials or synthetically produced and can then be polymerized to build a chain of two or more repeating units so that the repeating sequences form both the carrier and the immunogenic polypeptide. Alternatively, additional amino acids can be added to one or both ends of the *C. pneumoniae* polypeptide.

Alternative carriers are some substance, animal, vegetable, or mineral in origin, that is physiologically acceptable and functions to present the *C. pneumoniae* polypeptide to the immune system. Thus, a wide variety of carriers are acceptable, and include materials which are inert, or which have biological activity and/or promote an immune response. For example, an example of a protein carrier includes, but is not limited to, keyhole lympet protein, and hemocyanin. Polysaccharides can also be used as carriers, and include those of molecular weight 10,000 to 1,000,000, such as starches, dextran, agarose, ficoll, or it's carboxyl methyl derivative and carboxy methyl cellulose.

Polyamino acids are also contemplated for use as carriers, and these polyamino acids include, among others, polylysine, polyalanyl polylysine, polyglutamic acid, polyaspartic acid and poly ($C_2$–$C_{10}$) amino acids.

Organic polymers can be used as carriers, and these polymers include, for example, polymers and copolymers of amines, amides, olefins, vinyls, esters, acetals, polyamides, carbonates and ethers and the like. Generally speaking, the molecular weight of these polymers will vary dramatically. The polymers can have from two repeating units up to several thousand, e.g., two thousand repeating units. The number of repeating units will be consistent with the use of the immunizing composition in a host animal. Generally speaking, such polymers will have a lower molecular weight, say between 10,000 and 100,000 (the molecular weight being determined by ultracentrifugation).

Inorganic polymers can also be employed. These inorganic polymers can be inorganic polymers containing organic moieties. In particular, silicates and aluminum hydroxide can be used as carriers. It is preferred that the carrier be one which is an immunological adjuvant. In such cases, it is particularly contemplated that the adjuvant be muramyl dipeptide or its analogs.

The carrier can also be the residue of a crosslinking agent employed to interconnect a plurality of synthetic peptide containing chains. Crosslinking agents which have as their functional group an aldehyde (such as glutaraldehyde), carboxyl, amine, amido, imido or azidophenyl group. In particular, there is contemplated the use of butyraldehyde as a crosslinking agent, a divalent imido ester or a carbodiimide.

Chemical synthesis of peptides is described in the following publications: S. B. H. Kent, Biomedical Polymers, eds. Goldberg and Nakajima, Academic Press, New York, pp. 213–242, 1980; Mitchell et al., J. Org. Chem., 43, 2845–2852, 1978; Tam, et al., Tet. Letters, 4033–4036, 1979; Mojsov, A. R. Mitchell, and R. B. Merrifield, J. Org. Chem., 45, 555–560, 1980; Tam et al., Tet. Letters, 2851–2854, 1981; and Kent et al., Proceedings of the IV International Symposium on Methods of Protein Sequence Analysis, (Brookhaven Press, Brookhaven, N.Y. 1981.

In one embodiment, the method is provided for administering to a subject a therapeutically effective amount of a nucleic acid encoding a C. pneumoniae polypeptide, thereby treating or preventing the infection. In yet another embodiment, the method includes administering a therapeutically effective amount of a nucleic acid encoding a C. pneumoniae polypeptide, or a therapeutically effective amount of a C. pneumoniae polypeptide to generate an immune response against C. pneumoniae. Specific, non-limiting examples of an immune response are a B cell or a T cell response.

For administration of nucleic acids molecules, various viral vectors can be utilized. These vectors include adenovirus, herpes virus, vaccinia, or an RNA virus such as a retrovirus. In one embodiment, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated. By inserting a nucleic acid sequence encoding a C. pneumoniae polypeptide into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the polynucleotide encoding the C. pneumoniae peptide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. One colloidal system of this invention is a liposome. Liposomes are artificial membrane vesicles that are useful as delivery vehicles in vitro and in vivo. It has been shown that large uni-lamellar vesicles (LIN), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley et al., 1981, *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendotbelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

The present disclosure involves administering to a subject a therapeutically effective dose of a pharmaceutical composition containing a nucleic acid encoding a *C. pneumoniae* polypeptide, or the *C. pneumoniae* polypeptide itself, and a pharmaceutically acceptable carrier. Administering the pharmaceutical composition of the present invention may be accomplished by any means known to the skilled artisan. By subject is meant any mammal, including a human.

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science* 249:1527–1533, 1990, which is incorporated herein by reference.

The pharmaceutical compositions according to the invention may be administered locally or systemically. Amounts effective for therapeutic use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman and Gilman: The Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference.

For the use of *C. pneumoniae* polypeptides, effective doses of the therapeutic molecules will vary depending on the nature and severity of the condition to be treated, the age and condition of the patient and other clinical factors. Thus, the final determination of the appropriate treatment regimen will be made by the attending clinician. Typically, the dose range for a *C. pneumoniae* polypeptide will be from about 0.1 μg/kg body weight to about 100 mg/kg body weight. Other suitable ranges include doses of from about 1 μg/kg to 10 mg/kg body weight. The dosing schedule may vary from once a week to daily depending on a number of clinical factors, such as the subject's sensitivity to the *C. pneumoniae* peptide. In the case of a more aggressive disease it may be preferable to administer doses such as those described above by alternate routes including intravenously or intrathecally. Continuous infusion may also be appropriate.

For administration to animals, purified therapeutically active molecules are generally combined with a pharmaceutically acceptable carrier. Pharmaceutical preparations may contain only one type of therapeutic molecule, or may be composed of a combination of several types of therapeutic molecules. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As is known in the art, protein-based pharmaceuticals may be only inefficiently delivered through ingestion. However, pill-based forms of pharmaceutical proteins may be administered subcutaneously, particularly if formulated in a slow-release composition. Slow-release formulations may be produced by combining the target protein with a biocompatible matrix, such as cholesterol. Another possible method of administering protein pharmaceuticals is through the use of mini osmotic pumps. As stated above a biocompatible carrier would also be used in conjunction with this method of delivery.

The pharmaceutical compositions of the present invention may be administered by any means that achieve their intended purpose. Amounts and regimens for the administration of the therapeutic molecules can be determined readily by those with ordinary skill in the clinical art of treating diseases associated with C. pneumoniae infection. For use in treating these conditions, molecules are administered in an amount effective to inhibit C. pneumoniae replication. Typical amounts initially administered would be those amounts adequate to achieve tissue concentrations at the site of action which have been found to achieve the desired effect in vitro. The peptides or proteins may be administered to a host in vivo, for example through systemic administration, such as intravenous or intraperitoneal administration. Also, the peptides or nucleic acids may be administered intralesionally: i.e., the peptide or protein is injected directly into the pleural cavity.

EXAMPLES

Example 1

Material and Methods

Monoclonal

The 8A6 monoclonal antibody (mAb) was prepared previously at Center for Disease Control and Prevention (CDC) (Wong et al., 1992) using Renografin purified C. pneumoniae CWL 029 (ATCC VR-1310) as the immunogen. The primary 8A6 mAb producing cells were cultured in Isocoves Modified Dulbecco's Media (Gibco BRL Rockville, Md.) supplemented with 10% Low-IgG-FBS (Hyclone, Ogden, Utah). Cells were plated out into 96-well plates at $1\times10^4$ cells/mL in the first column. The cells are serially diluted 1:2. After 24 hours the plates were visually inspected for growth. The last well in each row with viable cells were selected, discarding wells with obvious multiple colonies. Wells with viable cells were expanded and supernatants harvested for testing by IFA. Reactive wells were further cloned in a similar fashion.

Subcloning was repeated three times to ensure single-cell clones. The most reactive clones were expanded. Expanded clones were then seeded at $1\times10^5$ cells/mL in IMDM+10% and allowed to grow for three days. Supernatants were harvested and tested for quantitative differences in antibody reactivity. The clone producing the highest concentration of reactive mAb based on IFA testing of clones was then weaned onto BD Cell media for generating large-scale antibody.

The 8A6 mAb producing cell line's growth and mAb production was scaled up using BD Cell medium (BD Pharmingen, San Diego, Calif.). The conditioned cells were transferred to roller bottles at a concentration of $2\times10^{-5}$ cells/mL in BD-Cell. Three days after inoculating cells were counted and the volume was adjusted to maintain $2\times10^{-5}$ cells/mL. The cells were incubated in roller-bottles at 37° C. in a 10% $CO_2$, humidified chamber for an additional 12 days. Cells were collected by centrifugation and the medium was carefully harvested without disrupting cell pellet.

Reactivity and species specificity of the mAbs selected were determined using indirect IFA with 3 *C. pneumoniae* (CWL011, CWL029, CWL050), 1 *C. trachomatis* (UW-F), and 2 *C. psittici* (DD34 and CP3) strains using standard protocols.

Sera

Human sera was obtained from healthy autologous volunteer donors at Emory University Hospital Blood Bank (Atlanta, Ga.).

Phage Library

The pIII phage library contains a random 15 amino acid insert located at the N-terminus of the pIII coat protein (Parmley & Smith 1988) and was constructed with the phage FUSE 5 vector (Smith & Scott 1993). The library was prepared by ligating a synthetic 45 bp BglII fragment into FUSE 5 (Smith and Scott, 1993) and transfecting it into *E. coli* K91/kan+ cells by electroporation.

Phage Preparation and Panning

After overnight growth, *E. coli* cells were removed by centrifugation, and the phage were precipitated overnight at 4° C. from the supernatant with a ⅕ volume of 20% polyethylene glycol-2.5 M NaCl. The phage were pelleted by centrifugation and resuspended in TBS (150 mM NaCl, 50 mM Tris-HCl, pH 7.5, 0.2% thimerosal). The phage titer was determined by making serial dilutions of a 100 μL total volume and adding 200 μL of early-log phase *E. coli* ER2537 cells. Aliquots of 100 μL were plated with 8 mL Luria-Bertani (LB) top agar, IPTG (isopropyl β-D-thiogalactoside) and X-gal (5-Bromo-4-chloro-3-indolyl-β-D-galactoside) on LB agar plates supplemented with tetracycline (15 mg/mL). After overnight growth at 37° C., the number of plaques was enumerated and the titer was calculated. A 50 μL aliquot of protein-G 4-Fast Flow™ sepharose (Amersham-Pharmacia Biotech, Piscataway, N.J.) slurry was washed 3 times in 0.1 M sodium carbonate buffer (pH 8.6) to remove the alcohol preservative. The protein-G sepharose was incubated with purified 8A6 mAb for 24 hr at 4° C. with gentle agitation. The remaining unreacted protein-G binding sites were blocked by incubation with either 10 mg/mL of bovine serum albumin (BSA) (Sigma Chemical Co., St. Louis, Mo.) or Superblock (Pierce Scientific, Rockford, Ill.) for at least 6 hours at 4° C. The sepharose was then pelleted and washed 10 times with Tris-buffered-saline containing BSA (1 mg/mL) and Tween 20 (0.05%) (TBST-B). The beads were stored in TBST-B in a final volume of 0.5 ml. For panning, $10^{-11}$ phage were added to 8A6-protein-G sepharose in a final volume of 1 ml in TBST-B. The binding mixture was incubated for 2 hr at room temperature with rocking to reach equilibrium. The beads were then washed 10 times with 1 mL of TBST. The bound phages were eluted from the beads by incubation with 1 mL of elution buffer (0.1 M glycine [pH 2.2], BSA [1 mg/mL], Tween 20 [0.05%]) for 10 min. The elution mixture was neutralized with 125 μL of 1 M Tris-HCl (pH 9.1). The phage titer of the elution mixture was determined as described above. The eluted phages were amplified by adding 150 μL of the neutralized elution mixture to 1 mL of *E. coli* ER2537 cells. After 30 min of incubation at room temperature, 25 ml of 2YT medium was added. The phages were precipitated as described above.

DNA Sequence of Selected Clones

Phage clones from the fourth round of biopanning were selected randomly, propagated and sequenced. Phage DNA was purified using QIAprep Spin M13 kit (Qiagen Inc. Valencia, Calif.) as per manufacturer's specifications and then ethanol precipitated. Sequencing reactions were performed using dRhodamine dye terminator cycle sequencing kit (Applied Biosystems, Fostercity, Calif.).

The specificities of the amplified products were confirmed by direct sequencing. The primer fd-tet.27.p: (5'-GTAG- CATTCCACAGACAGCCCTCATAG-3', SEQ ID NO:7) was used to sequence the PCR products. All PCR products were sequenced in both directions with the Prism® Dye-terminator Kit (Applied Biosystems Incorporated) using an ABI-Prism model 377 autosequencer (Applied Biosystems Incorporated). Sequenced products, DNA and translated amino acid sequences, were compared to C. pneumoniae sequences (TIGRE unfinished genome projects) available in GenBank (release 118) by using the FASTA algorithm implemented in Wisconsin Package Genetics Computer Group (GCG) as well as all sequences locally through the GCG package. Additional searches were run externally through the internet using BLAST (available at the NCBI website) FASTA-3 (located at the European Bioinformatics Institute (EBI) website, Hinxton, UK), EMBL (European Bioinformatics Institute website, Cambridge, UK), DDBJ (DNA Databank of Japan website, National Institute of Genetics, Shizuoka, JP), BLOCKS (Fred Hutchinson Cancer Research Center website, Seattle, Wash.), PRINTS (Protein Sequence Analysis Group website, Manchester, UK), PENDANT (Munich Information Center for Protein Sequences website, National Research Center for Environment and Health at the Max-Planck-Institut für Biochemie, Martin-sried, Germany), and additional search algorithms/methods found at ExPASy (Expert Protein Analysis System website) proteomics server of the Swiss Institute of Bioinformatics. For example, with FASTA-3, the search was performed using the BLOSUM3 matrix, with the parameters DNA STRAND=both, GAP PENALTIES, OPEN=-12. RESIDUE=-2, SCORES=50, ALIGNMENTS=50, KTUP=2, HIST=NO, in the PROTEIN database (PROTEIN-swall (SWALL non-redundant protein sequence database Swiss-sprot+Trembl+TremblNew)

Phage ELISA

A two-step phage enzyme-linked immunosorbent assay (ELISA) was performed to measure 8A6 phage affinity for 8A6 mAb. Immulon II-HB 96-well microtiter plates (Dynex Technologies, Chantily, Va.) were coated with purified 8A6 mAb (at 5 µg/ml) in 50 mM sodium carbonate (pH 9.6) at 4° C. overnight. The plates were then blocked with a solution of 3% nonfat skim milk (Difco, Detroit, Mich.) in Tris buffered saline (TBS)/Tween buffer (TBST-MK) for 2 hr at 37° C. Serial dilutions of the respective 8A6 phage clone stock were added to the wells and incubated for 2 hr at room temperature in TBST-MK at a final volume of 100 µL. The plates were then washed 4 times with TBS/tween buffer (TBST), and the bound phages were detected with a mouse anti-M13 polyclonal antibody conjugated to horseradish peroxidase (HRP) (Amersham Pharmacia Biotech, Piscataway, N.J.). Absorbance at 490 nm was recorded with an EIA reader (Bio-Tek Instruments Burlington, Va.). M13 phage without the 15-amino acid pIII insert was used as a negative control. To determine phage affinity, serial dilutions of 8A6 mAb and a subsaturating concentration of 4$^{th}$ round selected phage clone were added to wells in 100 µL of TBST-MK. After 2 hr at 37° C., the wells were washed 4 times with TBST, and bound phages were detected as described above.

Peptide ELISA

Three different plates were used to optimize peptide binding: Reacti-Bind maleic anhydride activated 96-well polystyrene microtiter plates (Pierce Scientific) (M-plate), Combiplate 8 streptavidin coated polystyrene microtiter plates (Labsystems, Franklin, Mass.) (S-plate), and immulon II-HB 96-well microtiter plates (Dynex Technologies) (I-plate). Protocols differed only in antigen coating and blocking procedures.

Briefly, M-plates were coated with purified 8A6 mAb (at 5 µg/ml) in 50 mM sodium carbonate (pH 9.6) at 37° C. for 1 hr. The M-plates were then blocked for one hour with a 1M glycine to eliminate any remaining unreacted maleic anhydride groups and then blocked with TBST-MK for 2 hr at room temperature. S-plates and I-plates were coated with purified 8A6 mAb (at 5 µg/ml) in 50 mM sodium carbonate (pH 9.6) at 4° C. overnight. The S-plates were then blocked with a solution of 10% Superblock (Pierce Scientific) in TBS/tween buffer (TBST-SB) for 2 hr at room temperature. The I-plates were blocked with TBST-MK for 2 hr at room temperature.

After the antigen has been immobilized on the respective plates, the ELISA format followed the same protocol. Briefly, the bound peptide was reacted with serially diluted 8A6 mAb having a starting dilution of 100 µg/mL and detected with a goat anti-mouse IgG H+L antibody HRP conjugate (Pierce Scientific). All washes were performed 4 times using TBST. Control peptides of dissimilar sequence were used as negative controls.

Peptide Synthesis

Biotinylated and non-biotinylated synthetic peptides were obtained from Bethyl Laboratories (Montgomery, Tex.). Resulting peptides were purified to ≧90% by high-pressure liquid chromatography. The amino acid sequences for the 8A6 mimiotope are as follows:

| | | |
|---|---|---|
| CP-8A6-A1 | RRLGRQTYDNES | SEQ ID NO:1 |
| CP-8A6-A2 | HDEGRQIIQFEE | SEQ ID NO:2 |
| CP-8A6-A3 | LRNCEQDFFTLN | SEQ ID NO:3 |
| CP-8A6-B1 | PNEPDDLALMRIIRI | SEQ ID NO:4 |
| CP-8A6-B3 | AFAQAPTHQLSL | SEQ ID NO:5 |
| CP-8A6-B10A | ESNPVDGAHLSL | SEQ ID NO:6 |

The peptides CP-8A6-A1 and CP-8A6-B3 were reconstituted at 1 mg/mL in sterile 200 µL 100 mM NaHCO$_3$ and peptides CP-8A6-A2, CP-8A6-A3, CP-8A6-B1 and CP-8A6-B10A were reconstituted at 1 mg/mL in 250 µL sterile 10% acetic acid and q.s. 1 mL.

Determination of mAb Isotypes

Isotype determinations were made using the Mouse Antibody Isotyping Kit (Gibco BRL) with the manufacturer's specified protocol. MAbs of known isotype were used as controls.

Immunodot Blot

Immunodot blot analyses were performed as previously described (Pau et al. 1988). Briefly, 5 µL of antigen was spotted onto nitrocellulose (Invitrogen, Carlsbad, Calif.), air-dried and blocked with casein-thimerasol buffer (CTB) (Kenna et al. 1985) for 0.5 hour. The blots were incubated with 8A6 mAb (1:1000) diluted in PBST. The blots were incubated for 2 hours at 37° C. with shaking and then washed 3 times in PBST for 5 minutes each wash. The blots were probed with goat anti-mouse IgG peroxidase conjugate (Pierce Scientific) for 1 hour at 37° C. with shaking. The blots were washed as before and developed using 3',3'-diaminobenzidine peroxidase substrate (Sigma Chemical Co. St. Louis, Mo.). The reaction was stopped by washing blots with deionized water.

Micro-Immunofluorescent Assay (MIF)

The 8A6 mAb was tested in the MRL Diagnostics (Cypress, Calif.) *Chlamydia pneumoniae* micro-immunofluorescent assay (MIF) (Wang, Grayston, Alexander, Holmes 1975, *J. Clin. Micro.* 1,250–55) IgG test following the manufacturer's recommendations.

IFA

The indirect immunofluorescence assay (IFA) was performed as described previously (Storey et al., 1993 and Wong Skelton Chan, 1992) with modifications. Antibiotic-free Buffalo African Green monkey cells were seeded into 1 dram shell vials or 24-well tissue culture trays containing 12 mm cover slips at a density of $3.0 \times 10^5$ cells/mL. Cells were incubated for 24 hours at 37° C. and checked for confluency. Cell cultures were infected by the addition of *C. pneumoniae* followed by centrifugation at 3000× g. Inclusions were counted using the Pathfinder® *Chlamydia* Culture Confirmation System staining kit (Sanofi Diagnostics Pasteur, Redmond, Wash.) as per manufacturer specifications. The 8A6 mAb was used as previously described (Wong et al. 1992) for detection of *C. pneumoniae* inclusions and to determine species specificity.

IFA Inhibition

A competitive inhibition IFA assay was performed using the previously described IFA assay with modification. The 8A6 peptide was serially diluted in a constant concentration of either 8A6 mAb or Pathfinder® detection reagent and incubated for 1 hour at room temperature. The material was then used to detect inclusions. Positive controls included 8A6 mAb and Pathfinder reagent without addition of peptide and negative controls included 8A6 mAb and Pathfinder reagent with addition of random, nonspecific peptides generated in the CDC peptide synthesis facility.

Example 2

Characterization of the 8A6 Monoclonal Antibody

The 8A6 monoclonal antibody (mAb) was previously developed by K. H. Wong at the Centers for Disease Control and Prevention (Wong et al., 1992) as a reagent for the detection of *C. pneumoniae* in cell culture using indirect IFA. The monoclonal yield was improved using standard cell culture techniques from <0.3 µg/mL reactive mAb to >1 mg/mL reactive mAb.

Reactivity was defined by assaying the mAb in an IFA assay using cultured *C. pneumoniae*. The mAb's specificity for *C. pneumoniae* was confirmed using the same assay with 3 other strains of *C. pneumoniae*. 1 strain of *C. trachomatis* and 2 strains of *C. psittici*. The mAb was further determined to be an $IgG_{2b}$ κ using 2 different commercially available typing kits.

Example 3

Selection of Phage

A phage display library expressing a linear, random 12-amino acid sequence (L12) and a phage library expressing a constrained cysteine-looped architecture 7 amino acid phage display library (C7) were used to select for peptides having the ability to bind the 8A6 mAb. A 12 amino acid library was selected based on the idea that a 12–15 amino acid length is similar in size to the complementary determining regions (CDR) in antibodies. The CDR has been shown to confer the ability to mimic many anti-idiotypic antibodies (Meloen, Puijk, & Slootstra 2000). The 7 amino acid phage display library having a cysteine constrained architecture was used to select for a target that may need additional conformational requirements. Using indirect ELISA, 150 phage clones from the L12 library having binding specificity for the target 8A6 mAb were identified. However, only ten clones from the C7 library were isolated and screened. The C7 library proved to be difficult to biopan the 8A6 mAb as amplification yields were poor (typically $>10^4$ pfu/mL versus the L12 library clones having yields in excess of $10^{14}$ pfu/mL) due to low binding as determined from indirect ELISA. The C7 library clones were subsequently removed from the peptide candidate pool.

The DNA encoding the displayed peptides from the 8A6-selected phages was sequenced. The DNA and subsequent amino acid sequences obtained from biopanning sorted into six groups having similar motifs and slightly variable base sequence and are represented by the peptides in Table 1.

TABLE 1

Peptides Isolated with the 8A6 monoclonal antibody

| peptide: | sequence: | | pI/average Mw: |
|---|---|---|---|
| CP-8A6-A1 | RRLGRQTYDNES | (SEQ ID NO:1) | 8.74/1494.59 |
| CP-8A6-A2 | HDEGRQIIQFEE | (SEQ ID NO:2) | 4.60/1500.59 |
| CP-8A6-A3 | LRNCEQDFFTLN | (SEQ ID NO:3) | 4.37/1499.66 |
| CP-8A6-B1 | PNEPDDLALMRIIRI | (SEQ ID NO:4) | 4.56/1766.09 |
| CP-8A6-B3 | AFAQAPTHQLSL | (SEQ ID NO:5) | 6.79/1283.45 |
| CP-8A6-B10A | ESNPVDGAHLSL | (SEQ ID NO:6) | 4.35/1238.32 |

The nucleotide and amino acid sequences of the phagotopes were used to search DNA and protein, motif and structural databases as described above. The sequences could not be matched with any significance or biological relevance to sequences or motifs currently known at this time. Since most of these search algorithms rely on linear sequence, a discontinuous epitope would be extremely difficult to identify. The sequences of the epitopes identified here did not match significantly with any known sequences currently in the many databases searched including the unfinished genomes of *Chlamydophila* and *Chlamydia* species, it is therefore likely that the 8A6 epitope is a discontinuous epitope. However, as all of these epitopes specifically bind antibody, these epitopes could be used in assays, or as immunogenic compositions, in linear form.

Example 4

Reactivity by ELISA of Phage Clones with 8A6 mAb

Figure 2:
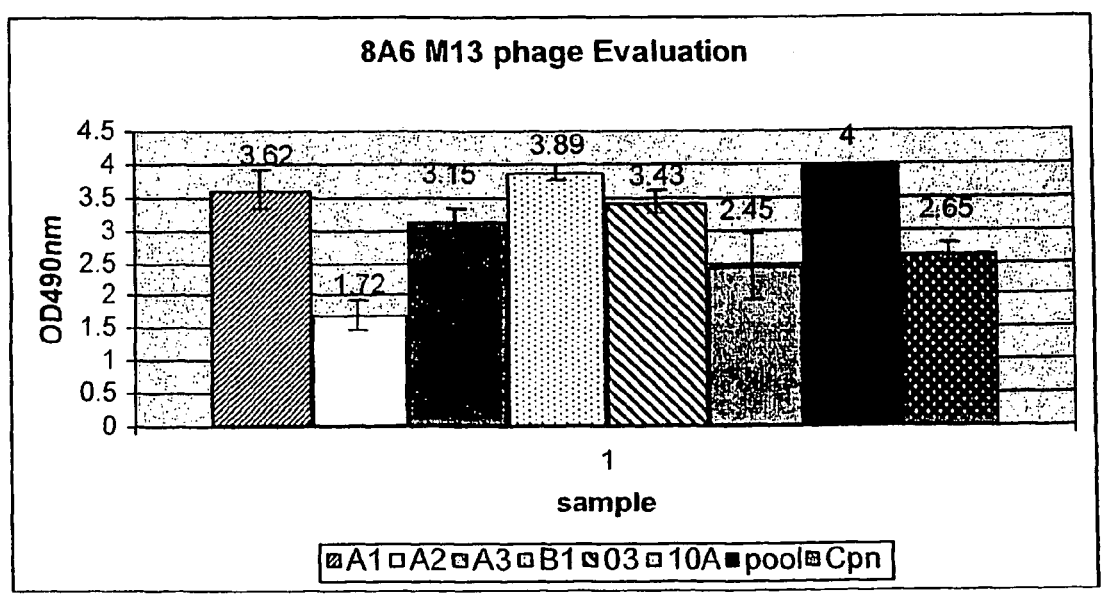
FIG. 2 is a bar graph showing the reactivity of 8A6 mAb by ELISA using phagotopes selected by screening with 8A6, in optical density units ($OD_{490nm}$) given on the y-axis where columns represent phage reactivity. Wild type phage was used as the negative control (−).

To demonstrate the specificity of phage binding to the 8A6 mAb (IgG), ELISA plates were coated with the 8A6 mAb, the immobilized mAb was incubated with representative phage clones from each selection ($10^{10}$ pfu/well), and binding was measured (FIG. 2). The selected phage clones bound to the 8A6 mAb at optical density levels of >3.0 (on a scale of 0 to 4) as compared to <0.8 observed with the wild-type parental phage. The 8A6 phage clones having the highest optical density were also screened for binding to heterologous mAbs (7D10, 3F12, 3G9.1 (genus specific) and anti-biotin mAbs). The 8A6 phage clones selected did not demonstrate any ability to specifically bind to other anti-*C. pneumoniae* monoclonal antibodies for which they were not selected against (Pathfinder reagent).

The nucleotide and amino acid sequences of the phagotopes were used to search DNA and protein, motif and structural databases as described above. The sequences could not be matched with any significance or biological relevance to sequences or motifs currently known at this time. Since most of these search algorithms rely on linear sequence, a discontinuous epitope for which one had sequence for would be extremely difficult to identify. The sequences of the epitopes identified here did not match significantly with any known sequences currently in the many databases searched including the unfinished genomes of *Chlamydophila* and *Chlamydia* species, it is therefore likely that the 8A6 epitope is a discontinuous epitope.

Example 5

Phage and Peptides Block the Binding of Ab to *C. pneumoniae* in ELISA and IFA

The ability to demonstrate the specific recognition of the selected peptide sequence by the selecting mAb using competitive inhibition assays is a good indication that the selected phage binds to the antibody's variable regions. However, to demonstrate that the displayed sequence actually resembles the target epitope for which the 8A6 mAb binds, it was necessary to demonstrate the ability to block the mAb binding to the *C. pneumoniae* antigen. To perform these experiments, an ELISA was utilized in which mAb and inhibitor (phage) were premixed, incubated for 2 hours, and then plated onto the microtiter plates with renographin purified, sonicated whole-cell *C. pneumoniae*. Inhibition of the mAb's binding to the respective lysate indicated that the phage was successfully competing with the lysate for mAb binding.

Figure 3A:
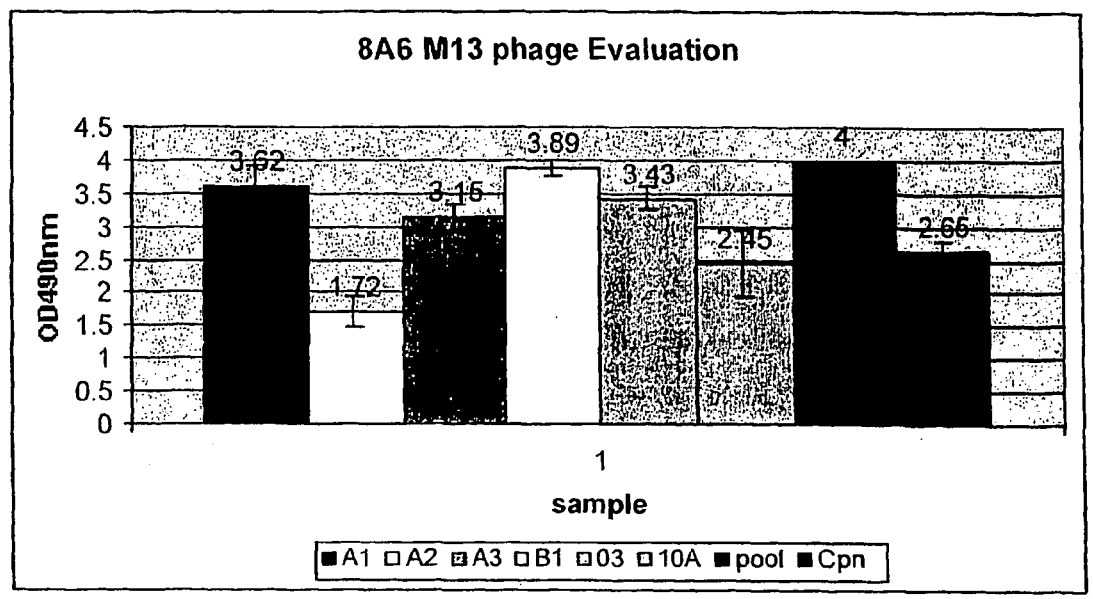
FIG. 3 is a bar graph showing a comparison of relative reactivity of peptide and phage expressing the respective peptide.
Figure 3B:
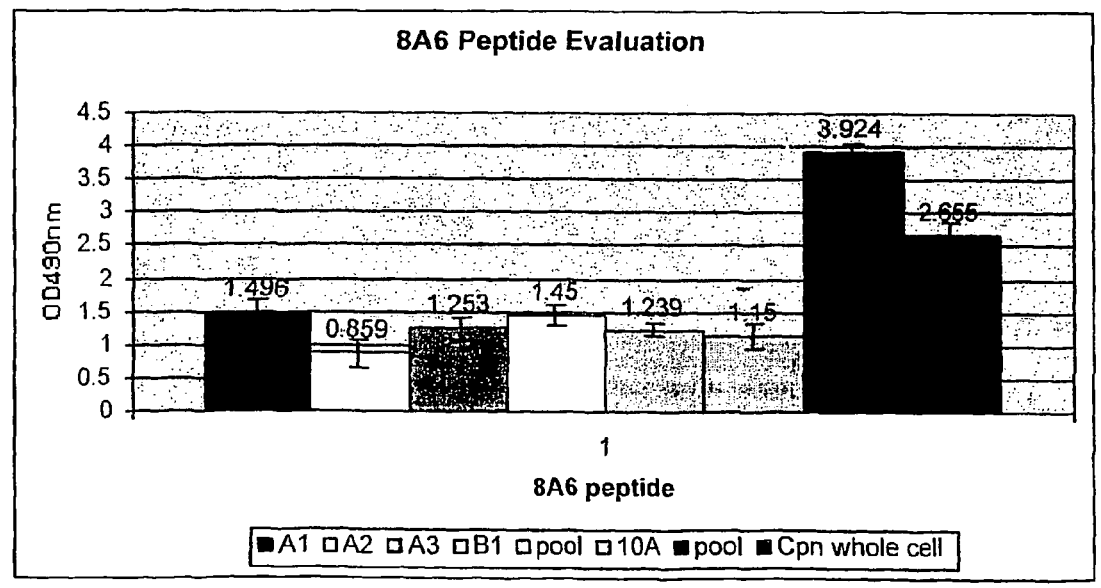

Since the phage clones demonstrated specific binding to 8A6 and ability to compete against sonicated native *C. pneumoniae* material, peptides were synthesized to determine if the binding of synthetic peptide had similar or equivalent binding to the respective mAb target (FIG. 3). Several methods were used to determine binding specificity. Using a direct ELISA, the synthetic peptides demonstrated equivalent binding to their respective mAb. The best synthetic peptides were selected by competing the peptide against the respective native *C. pneumoniae* lysate for binding to the target mAb. The peptides demonstrating the best binding as determined by the percent inhibition and $IC_{50}$ were CP-8A6-B1, CP-8A6-A3, CP-8A6-A2, and CP-8A6-A1, respectively.

TABLE 2

Percent inhibition and 50% Inhibiting Concentration ($IC_{50}$) from competitive inhibition ELISA

| peptide | percent inhibition | $IC_{50}$ (µg/mL) |
| --- | --- | --- |
| CP-8A6-A1 (SEQ ID NO: 1) | 84.5% | 4.82 |
| CP-8A6-A2 (SEQ ID NO: 2) | 83.5% | 18.29 |
| CP-8A6-A3 (SEQ ID NO: 3) | 95.1% | 18.54 |
| CP-8A6-B1 (SEQ ID NO: 4) | 95.44% | 2.93 |
| CP-8A6-B3 (SEQ ID NO: 5) | 67.8% | 6.46 |
| CP-8A6-B10A (SEQ ID NO: 6) | 57.4% | 18.90 |

Various concentrations of peptide were used to inhibit binding of 8A6 mAb to sonicated *C. pneumoniae* fixed to solid phase, as indicated.

The peptide CP-8A6-B1 was able to able to inhibit in a dose-dependent manner, with 95.44% at 50 µg/mL and 50% at 2.93 µg/mL of peptide, indicating that in solution under the conditions used, the peptide could act as an inhibitory mimotope of the 8A6 mAb (FIG. 1). Using an indirect IFA, the CP-8A6-B1 peptide demonstrated the ability to completely block any observable binding of 8A6 mAb to fixed, cultured *C. pneumoniae* cells (RBs and EBs) until a dilution a peptide concentration of 100 ng/mL was reached. Due to the subjective nature of IFA tests, it is difficult to standardize a competitive inhibition to obtain fluorescence measures. Instead, slides were scored from 1 to 4 such that a value of 3+ equals the endpoint titer and changes due to inhibition were scored empirically from comparison with control slides. The 8A6 mAb did not demonstrate the ability to bind to the proprietary antigen target presented in a commercial MIF kit. Thus, a comparison of the indirect IFA with a commercially available MIF assay was not performed.

Example 6

Binding of Human Anti-*C. pneumoniae* Antibodies to Peptide

Figure 4:
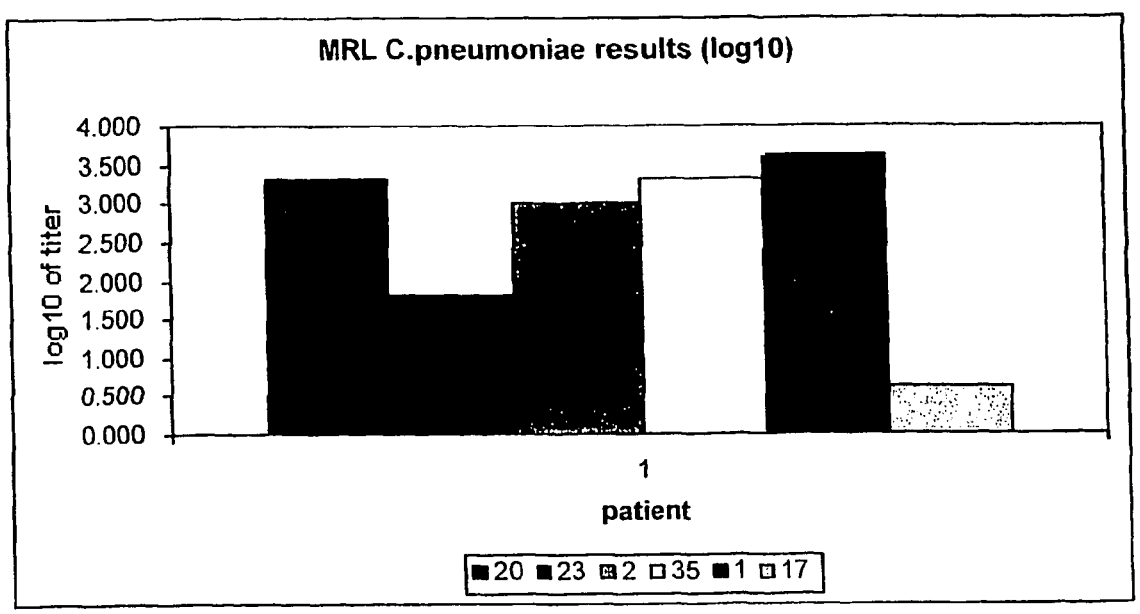
FIG. 4 is a bar graph showing a comparison of relative reactivity of peptide in ELISA assay to MRL *C. pneumoniae* test assay using the 6 patient sera.

To determine if the epitope identified from the murine mAb was similar to ally epitopes found in humans, normal human sera were obtained from a blood bank repository. The sera had been screened previously for *C. pneumoniae* using MIF. Using direct ELISA and a modified slot-blot, the human sera demonstrated the ability to bind to the peptides. The slot-blot was used to quickly check for binding of the antibody to the various peptides. Though the assay is qualitative, it was able to demonstrate the ability of the human sera to bind to the peptide. The data obtained from the peptide ELISA was compared to a direct ELISA using the sonicated *C. pneumoniae* as a target. The data were compared to data sets obtained from MIF and flow cytometry using the same acute and convalescent sera (artificial nomenclature based upon 4 week interval between serum draws). There is agreement among the sets of data in that if sera had a high or low endpoint titer with MIF these titers were similarly reflected in the endpoints observed with the peptide ELISA (FIG. 4). The geometric mean titers (GMT) observed using MIF, flow cytometry and peptide ELISA were 362.04, 181.02, and 102.23, respectively.

In spite the growing significance of *C. pneumoniae* as an emerging pathogen, the lack of any standardized and fully validated diagnostic methods including serology has previously made it very difficult for investigators to identify *C. pneumoniae* in clinical specimens. It is interesting to note that only the TWAR serovar has been observed for clinically isolated *C. pneumoniae* using current tests, though there are several reports demonstrating ample antigenic variation (Black et al., 1990; Black et al., 1991; Shirai et al., 2000; Knudsen et al., 1999). Other *Chlamydia* and *Chlamydophila* species are known to have numerous serologically distinct strains (Grayston 2000). A number of investigators have found differences in not only the variable regions of OMP1 (Molestina et al. 1998; Gaydos, Quinn, Bobo, Eiden 1992) but also in several other outer membrane localized proteins (OMPs) including ompA and porB, another 10 predicted omp genes, and 27 pmp genes (e.g., Black et al, 1990). The observed differences appear to be strain specific. For example, a comparative study of the OMPs of the two strains CWL029 (isolated at CDC in 1987) and J138 (isolated in Japan in 1994) revealed a nucleotide sequence identity of 89.6%–100% and a deduced amino acid sequence identity of 71.1%–100%. The level of diversity observed by comparing individual gene sequences or protein profiles, though modest, might be expected especially given recent comparative studies of the full genomes of strains J138 and CWL029 and empiric size differences in the J138, CWL029, and AR39 genomes whose circular chromosomes consists of 1226565 bp, 1230230 bp (Genbank accession # AE001363) and 1069412 bp (Genbank accession # AE002161), respectively. The organization of the J138, CWL029, and AR39 genomes, gene order and predicted protein families are very similar, suggesting structural and functional conservation amongst the three unrelated isolates (Shirai et al. 2000).

Mice immunized with *C. pneumoniae* produce sera have very different reaction patterns by Western blot then sera collected from patients having a previous *C. pneumoniae* infection. While mice produce sera reactive to similar antigens in *C. pneumoniae* and *C. trachomatis*, the human response to *C. pneumoniae* antigens appears to be very conserved and less diverse. Additionally, serologic responses of humans infected with *C. pneumoniae* differ markedly from those humans who were infected with *C. trachomatis* or *C. psittici*. This perhaps can best be seen in the MOMP protein, which is a major surface exposed immunogen of *C. trachomatis* and *C. psittici*, but not a major immunogen of *C. pneumoniae*.

One of the previous difficulties in other protocols using *C. pneumoniae* antigens is the evidence pointing to labile conformational epitopes (Knudson et al. 1999). The implementation of phage display as a tool to identify an interaction between target molecule and a receptor molecule under native conditions avoids some of the previously encountered difficulties with labile *C. pneumoniae* epitopes. As described herein, two phage display libraries were utilized to identify the epitope of the 8A6 mAb. The 8A6 mAb was determined to have specific reactivity to *C. pneumoniae* without any detectable cross-reaction with *C. trachomatis* or *C. psittici* antigens. A set of peptides was identified that have reactivity using an ELISA with the 8A6 mAb and yet that have no linear sequence identities with any currently known protein or DNA sequences. The peptides, though dissimilar in sequence, might have an architectural motif as CP-8A6-A1 has several helix breaking amino acids in its sequence. These residues could effectively kink the linear peptide. CP-8A6-B1 has a disproportionate amount of hydrophobic residues mixed with charged residues (1:2 ratio), possibly allowing the shaping of the peptide with hydrophobic-hydrophobic and hydrophilic-hydrophilic interactions. However, it should be noted that the conformation of peptides is dependent upon solvent and concentration effects. High dilutions of peptide will have limited intermolecular interactions and hence these interactions will have limited influence on conformation.

In the present study, phage expressing-a constrained 7 amino acid loop bound by a disulfide bond did not react very well with the 8A6 mAb. However, the constrained library used is only one possible means of introducing controlled structure. Additional methods include binding to carrier proteins or defined protein domains.

The peptide mimotopes identified were able to bind to antibodies found in human sera that appear to be directed to *C. pneumoniae*. Though the 8A6 mAb reacts with the phage mimotopes, peptide mimotopes, cells infected with *C. pneumoniae* (IFA) and whole cell lysates of *C. pneumoniae*, it did not react with the commercial MIF antigen or with formalin fixed elementary bodies. This suggests that, under denaturing conditions, the epitope that the 8A6 mAb binds can be destroyed or rendered inaccessible such that the mAb is no longer able to effectively bind.

Thus, a random peptide display libraries was screened with the mAb 8A6, raised against *C. pneumoniae* and peptides were identified that contain discontinuous motifs not yet identified in sequence databases yet strongly inhibit the reactivity of 8A6 with native *C. pneumoniae* in both an ELISA and indirect IFA formats. The peptide mimotopes presumably express important contact residues and intermolecular interactions for the binding of 8A6 to the unknown *C. pneumoniae* epitope. The unique sequence and specificity of the peptides open up new avenues of investigation for standardized assays, immunizing compositions, and vaccine development Example 7

Generation of CP-8A6-B1 Immune Response in Naïve Mice and Rabbits

In order to identify immunologically reactive *C. pneumoniae* peptides that can be used in the development of a *C. pneumoniae* vaccine, naive mice and rabbits were immunized with various *C. pneumoniae* polypeptides. An exemplary protocol is as follows: 50–200 µg of CP-8A6-B1 (SEQ ID NO:4) was mixed with 1 mg of aluminum hydroxide, a less inflammatory alternative to Freund's adjuvant. Rabbits were injected subcutaneously at multiple sites with 0.05 ml of inoculum, whereas mice were immunized intraperitoneally with no more than 0.2 ml of inoculum. At least 2–3 weeks following the initial immunization, the mice and rabbits were given their first booster immunizations. Mice were given subsequent boosters at two week intervals for up to 6 total injections, whereas rabbits were typically injected every 4–6 weeks. Sera collected from the mice and rabbits were tested for their reactivity to CP-8A6-B1 by ELISA. Immulon II-HB 96 well microtiter plates (Dynex Technologies) were coated with purified CP-8A6-B1 (at 5 µg/ml) in 50 mM sodium carbonate (pH 9.6) at 4° C. overnight. The plates were then blocked with Tris-buffered saline, Tween 20 buffer with 3% nonfat skim milk (TBST-MK) for 2 hours at room temperature. Briefly, after the antigen was immobilized, the bound peptide was tested with serial dilutions of the mouse and rabbit antisera and was detected with a goat anti-mouse IgG or a goat anti-rabbit IgG heavy plus light chain antibody horseradish peroxidase conjugate (Pierce Scientific). All washes were performed four times using Tris-buffered saline, Tween 20 buffer. Absorbance at 490 nm was recorded with an enzyme immunoassay reader (Bio-Tek Instruments, Burlington, Vt.). Control peptides of dissimilar sequences were used as negative controls. Wells with optical density readings greater than 0.2 units at 490 nm were indicative of an immunologically reactive antiserum. ELISA analysis demonstrated that both mice and rabbits produced an immune response to CP-8A6-B 1.

Example 8

Mouse Lung Challenge Model to Identify Peptides that Protect Against *C. pneumoniae* Infection A mouse lung challenge model is used to further identify *C. pneumoniae* peptides that can elicit a protective response in mice (see Murdin et al., J. Infect. Dis. 181 (suppl. 3): S544–51, 2000, herein incorporated by reference). Mice are immunized both intramuscularly and intranasally with plasmid DNA encoding the peptides listed in Table 1 (SEQ ID NOs: 1–6). For example, anesthetized mice aspirate 50 µl of phosphate buffered saline (PBS) containing 50 µg of DNA at 0, 3, and 6 weeks. At the same time, alternate left and right quadriceps are injected with 100 µg of DNA in 50 µL of PBS so that each mouse receives 150 µg of DNA at each time.

Alternatively, the mice can be immunized with the peptides themselves (SEQ ID NOs: 1–6). Control animals are mock immunized with PBS. Eight weeks post-immunization, the mice are challenged with a dose of *C. pneumoniae*. For example, *C. pneumoniae* strains AR-39, CM-1, and CWL-029 are purchased from the American Type Culture Collection (Rockville, Md.) and cultured on LH cells (University of Washington, Seattle) using MEM with 1.25% fetal bovine serum and 1 μg/ml cycloheximide. Challenge inocula for animal studies are prepared by inoculating HL cell moolayers in T25 flasks (Nunc, Rochester, N.Y.) with *C. pneumonia* at a multiplicity of infection (MOI) of about 1, centrifuging the chlamydia onto the cells at 1350 g for 1 hour at room temperature, and culturing at 35° C. for four to five days. The cell monolayer is then washed and harvested by scraping into 0.5 mL sucrose phosphate glutamate (SPG) buffer (sucrose, 60 g; $KH_2PO_4$, 0.415 g; $Na_2HPO_4$, 0.976 G; glutamic acid, 0.576 g in 1 liter of distilled water, pH 7.5), sonicated to release intracellular elementary bodies, clarified by low-speed centrifugation, and aliquoted and stored frozen at −70° C. For a challenge inocula, clarified culture harvests are diluted in SPG specific times post-infection, for example at days 1, 2, 4, 7, 9, 11, 14, and 22, the mice are euthanized and the lungs are harvested to measure infectivity and interferon-γ expression.

In order to measure *C. pneumoniae* titers in the harvested lung tissues, a portion of the mouse lung is homogenized and aliquots of the homogenate, serially diluted in Iscove's medium, are used to inoculate HL cell monolayers in 24 well plates. Inoculated cells are incubated for 3 days at 35° C. Infected cells are fixed and *C. pneumoniae* detected by incubation with an anti-*C. pneumoniae* primary antibody, followed by incubation with a secondary antibody conjugated to a detectable marker. The average number of inclusion-forming units (ifu) per lung is counted and the lung tissue is analyzed for protection from *C. pneumoniae* infection as a function of the number of inclusion forming units for that lung.

In order to measure interferon-y expression, total RNA is isolated from the harvested lung tissue using TRIzol (Gibco Life Technologies), as described by the manufacturer, and the RNA is used in an RT-PCR assay. Expression of interferon-γ is compared to the number of inclusion-forming units (ifu) per lung and is a measure of the ability of the lung to elicit a protective immune response.

The time-course of *C. pneumoniae* lung infection and RT-PCR of interferon-γ demonstrate that the *C. pneumoniae* peptides protect mice from *C. pneumoniae* infection. Thus, inoculation with at least one of the peptides listed in Table 1 causes a reduction in bacteria burden as compared to controls. In addition, the level of interferon-γ varies over time with the changes in bacteria burden. A peak is found coincident with expression of host resistance and resolution of infection.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

REFERENCES

1. Aldous et al., 1990. *Chlamydia pneumoniae* strain TWAR infection in Seattle children and their families 1965–79, p. 437–440. In Bowie et al., (eds.), *Chlamydial* infections: proceedings of the Seventh international Symposium on Human Chlamydial Infections, Harrison Hot Springs, British Columbia, Canada, 24–29 Jun. 1990. Cambridge University Press, New York.

2. Barnes, 1989. Laboratory diagnosis of human chlamydial infections. Clin Microbiol Rev. 2(2):119–36.

3. Black et al., 1990. Antigenic variation in *Chlamydia pneumoniae,* p. 410–413. In Bowie et al., (eds.), Chlamydial infections proceedings of the Seventh International Symposium on Human Chlamydial Infections, Harrison Hot Springs, British Columbia, Canada, 24–29 Jun. 1990. Cambridge University Press, New York.

4. Black et al., 1991. Antigenic variation among strains of *Chlamydia pneumoniae.* J Clin Microbiol. 29(7):1312–6.

5. Brade et al., 1990. Characterization of murine monoclonal and murine, rabbit, and human polyclonal antibodies against chlamydial lipopolysaccharide. Infect Immun. 58(1): 205–13.

6. Chirgwin et al., 1991. Infection with *Chlamydia pneumoniae* in Brooklyn. J Infect Dis. 163(4):757–61.

7. Everett et al., 1999. Emended description of the order *Chlamydiales*, proposal of *Parachlamydiaceae fam. nov.* and *Simkaniaceae fam. nov*., each containing one monotypic genus, revised taxonomy of the family *Chlamydiaceae*, including a new genus and five new species, and standards for the identification of organisms. Int J Syst Bacteriol. 49 Pt 2:41540.

8. Gaydos et al., 1992. Simiarity of *Chlamydia pneumonia* strains in the variable domain IV region of the major outer membrane protein gene. Infect Immun. 60(12):5319–23.

9. Genetics_Computer_Group. 2001. Wisconsin Package Version, 10.0.1 ed. Genetics Computer Group, Madison, Wis.

10. Gnarpe et al., 1999. Evidence of 2 waves of *Chlamydia pneumoniae* infection in Gavle, Sweden, 1990–96. Scand J Infect Dis. 31(1):83–6.

11. Grayston, J. T. 2000. Background and current knowledge of *Chlamydia pneumoniae* and atherosclerosis. J Infect Dis. 181 Suppl 3:S402–10.

12. Grayston, J. T. 1994. *Chlamydia pneumoniae* (TWAR) infections in children. Pediatr Infect Dis J. 13(8):675–84; quiz 685.

13. Grayston, J. T. 1992. Infections caused by *Chlamydia pneumoniae* strain TWAR. Clin Infect Dis. 15(5):757–61.

14. Grayston et al., 1990. A new respiratory tract pathogen: *Chlamydia pneumoniae* strain TWAR. J Infect Dis. 161(4):618–25.

15. Grayston et al., 1989. Community- and hospital-acquired pneumonia associated with *Chlamydia* TWAR infection demonstrated serologically. Arch Intern Med. 149 (1): 169–73.

16. Hahn et al., 2000. Serologic markers for *Chlamydia pneumoniae* in asthma. Ann Allergy Asthma Immunol. 84(2):227–33.

17. Haidl et al., 1992. Guillain-Barre syndrome after *Chlamydia pneumoniae* infection. N Engl J Med. 326(8): 576–7.

18. Hannu et al., 1999. *Chlamydia pneumoniae* as a triggering infection in reactive arthritis. Rheumatology (Oxford). 38(5):411–4.

19. Jokinen et al., 2001. Microbial Etiology of Community-Acquired Pneumonia in the Adult Population of 4 Municipalities in Eastern Finland. Clin Infect Dis. 32(8): 1141–1154.

20. Knudsen et al., 1999. Identification of two novel genes encoding 97- to 99-kilodalton outer membrane proteins of *Chlamydia pneumoniae* Infect Immun. 67(1):375–83.

21. Laurila et al., 1997. *Chlamydia pneumoniae* and chronic lung diseases. Scand J Infect Dis Suppl. 104:34–6.

22. Miyashita et al., 1996. Continuous isolation and characterization of *Chlamydia pneumoniae* from a patient with diffuse panbronchiolitis. Microbiol Immunol. 40(8): 547–52.

23. Molestina et al., 1998. Characterization of a strain of *Chlamydia pneumoniae* isolated from a coronary atheroma by analysis of the omp1 gene and biological activity in human endothelial cells. Infect Immun. 66(4): 1370–6.

24. Normann et al., 1999. Demonstration of *Chlamydia pneumoniae* in cardiovascular tissues from children with Kawasaki disease. Pediatr Infect Dis J. 18(1):72–3.

25. Ouchi et al., 1994. Prevalence of *Chlamydia pneumoniae* in acute lower respiratory infection in the pediatric population in Japan. Acta Paediatr Jpn. 36(3):256–60.

26. Porath et al., 1997. The epidemiology of community-acquired pneumonia among hospitalized adults. J Infect. 34(1):41–8.

27. Ramirez, J. A. 1996. Isolation of *Chlamydia pneumoniae* from the coronary artery of a patient with coronary atherosclerosis. The *Chlamydia pneumoniae*/Atherosclerosis Study Group. Ann Intern Med. 125(12):979–82.

28. Schito et al., 1994. Incidence of lower respiratory tract infections caused by *Mycoplasma, Chlamydia* and *Legionella:* an Italian Multicenter Survey. J Chemother. 6(5):319–21.

29. Shirai et al., 2000. Comparison of whole genome sequences of *Chlamydia pneumoniae* J138 from Japan and CWL029 from USA. Nucleic Acids Res. 28(12):2311–4.

30. Shirai et al., 2000. Comparison of outer membrane protein genes omp and pmp in the whole genome sequences of *Chlamydia pneumoniae* isolates from Japan and the United States. J Infect Dis. 181 Suppl 3:S524–7.

31. Sriram et al., 1999. *Chlamydia pneumoniae* infection of the central nervous system in multiple sclerosis. Ann Neurol. 46(1):6–14.

32. Storey et al., 1993. Evidence for *Chlamydia pneumoniae* of non-human origin. J Gen Microbiol. 139(Pt 11): 2621–6.

33. Verkooyen et al., 1997. Diagnosis of *Chlamydia pneumoniae* infection in patients with chronic obstructive pulmonary disease by micro-immunofluorescence and ELISA. J Med Microbiol. 46(11):959–64.

34. Verkooyen et al., 1998. Evaluation of PCR, culture, and serology for diagnosis of *Chlamydia pneumoniae* respiratory infections. J Clin Microbiol. 36(8):2301–7.

35. Wang et al., 1975. Simplified microiminunofluorescence test with trachoma-lymphogranuloma venereum (*Chlamydia trachomatis*) antigens for use as a screening test for antibody. J Clin Microbiol. 1(3):250–5.

36. Wong et al., 1992. Efficient culture of *Chlamydia pneumoniae* with cell lines derived from the human respiratory tract. J Clin Microbiol. 30(7):1625–30.

37. Wubbel et al., 1999. Etiology and treatment of community-acquired pneumonia in ambulatory children. Pediatr Infect Dis J. 18(2):98–104.

38. Messmer et al., 2001, Comparison of two commercial micro-immunofluorescence kits and an enzyme immunoassay kit for detection of serum immunoglobulin G antibodies to *Chlamydia pneumoniae* Clin. Diagn. Lab. Immunol. 8(3):588–92

---

We claim:

1. An isolated peptide consisting of at least eight consecutive amino acids of the amino acid sequence set forth as SEQ ID NO:1, SEQ ID NO:2, SEQ ID NO:3, SEQ ID NO:4, SEQ ID NO:5, or SEQ ID NO:6.

2. The peptide of claim 1, wherein the peptide consists of the amino acid sequence set forth as SEQ ID NO:1, SEQ ID NO:2, SEQ ID NO:3, SEQ ID NO:4, SEQ ID NO:5, or SEQ ID NO:6.

3. The peptide of claim 1, covalently linked to a carrier protein.

4. The peptide of claim 1, consisting of the amino acid sequence set forth as SEQ ID NO:1, SEQ ID NO:2, SEQ ID NO:3, SEQ ID NO:4, SEQ ID NO:5, and SEQ ID NO:6.

5. A composition, comprising: an isolated peptide consisting of the amino acid sequence set forth as SEQ ID NO:1, SEQ ID NO: 2, SEQ ID NO:3, SEQ ID NO:4, SEQ. ID NO:5, or SEQ ID NO:6; and a pharmaceutically acceptable carrier.

6. The composition of claim 5, wherein the peptide consists of the amino acid sequence set forth as SEQ ID NO: 1.

7. The composition of claim 5, wherein the peptide consists of the amino acid sequence set forth as SEQ ID NO:2.

8. The composition of claim 5, wherein the peptide consists of the amino acid sequence set forth as SEQ ID NO:3.

9. The composition of claim 5, wherein the peptide consists of the amino acid sequence set forth as SEQ ID NO:4.

10. The composition of claim 5, wherein the peptide consists of the amino acid sequence set forth as SEQ ID NO:5.

11. The composition of claim 5, wherein the peptide consists of the amino acid sequence set forth as SEQ ID NO:6.

12. A method for the determining the presence of an antibody in a sample that binds to *C. pneumoniae* peptide antigen, comprising: binding an isolated peptide consisting of at least eight consecutive amino acids of the amino acid sequence set forth as SEQ ID NO:1, SEQ ID NO: 2, SEQ ID NO:3, SEQ ID NO:4, SEQ ID NO:5, or SEQ ID NO:6 to a solid substrate; contacting the sample with the peptide to form an antigen-antibody complex; and detecting the presence of the antibody-antigen complex, wherein the presence of the complex determines the presence of the antibody in the sample.

13. The method of claim 12, wherein the detection of the antibody-antigen complex comprises contacting the antibody-antigen complex with a labeled antibody that specifically binds the antibody-antigen complex.

14. The method of claim 13, wherein the label is a radiolabel, a fluorescent label, or an enzymatic label.

15. The method of claim 12, wherein the antibody is in a biological sample.

16. The method of claim 15, wherein the sample is a serum, blood, cell, tissue, or pleural fluid sample.

* * * * *